(12) United States Patent
Hwang et al.

(10) Patent No.: US 9,199,891 B2
(45) Date of Patent: Dec. 1, 2015

(54) PROCESS FOR REDUCING THE BENZENE CONTENT OF GASOLINE

(75) Inventors: Shyh-Yuan H. Hwang, Needham, MA (US); Ronald Birkhoff, Houston, TX (US); Richard F. Guarino, Fairhaven, MA (US); J. Erik Moy, South Grafton, MA (US); Joseph C. Peters, Quincy, MA (US)

(73) Assignee: BADGER LICENSING LLC, Boston, MA (US)

( * ) Notice: Subject to any disclaimer, the term of this patent is extended or adjusted under 35 U.S.C. 154(b) by 294 days.

(21) Appl. No.: 13/982,964

(22) PCT Filed: Nov. 30, 2011

(86) PCT No.: PCT/US2011/062648
§ 371 (c)(1),
(2), (4) Date: Aug. 23, 2013

(87) PCT Pub. No.: WO2012/108926
PCT Pub. Date: Aug. 16, 2012

(65) Prior Publication Data
US 2013/0324776 A1   Dec. 5, 2013

Related U.S. Application Data

(63) Continuation of application No. PCT/US2011/023912, filed on Feb. 7, 2011.

(51) Int. Cl.
*C07C 2/66* (2006.01)
*C07C 2/64* (2006.01)

(52) U.S. Cl.
CPC ........................ *C07C 2/64* (2013.01)

(58) Field of Classification Search
USPC ........................... 585/447, 449, 467
See application file for complete search history.

(56) References Cited

U.S. PATENT DOCUMENTS

| | | | |
|---|---|---|---|
| 3,775,483 A | 11/1973 | Frederickson et al. | |
| 4,343,957 A | 8/1982 | Sartorio et al. | |
| 4,393,262 A | 7/1983 | Kaeding | |
| 4,891,458 A | 1/1990 | Innes et al. | |
| 4,950,823 A | 8/1990 | Harandi et al. | |
| 5,149,894 A | 9/1992 | Holtemann et al. | |
| 5,491,270 A | 2/1996 | Chin et al. | |
| 5,545,788 A | 8/1996 | Cheng et al. | |
| 6,008,422 A | 12/1999 | Schulz et al. | |
| 6,835,862 B1 | 12/2004 | Gajda et al. | |
| 7,476,774 B2 | 1/2009 | Umansky et al. | |
| 7,652,181 B1 * | 1/2010 | Schmidt et al. | 585/323 |
| 2006/0194999 A1 | 8/2006 | Brown et al. | |
| 2008/0171900 A1 | 7/2008 | Scmidt | |
| 2010/0210886 A1 | 8/2010 | Brown et al. | |
| 2010/0249472 A1 | 9/2010 | Clark et al. | |
| 2010/0300930 A1 | 12/2010 | Clark et al. | |

FOREIGN PATENT DOCUMENTS

| | | |
|---|---|---|
| EP | 0485683 A1 | 11/1990 |
| WO | 2012108861 A1 | 8/2012 |
| WO | 2012108924 A1 | 8/2012 |
| WO | 2013028215 A1 | 2/2013 |

OTHER PUBLICATIONS

Laredo G C et al.: "Benzene reduction in gasoline by alkylation with olefins: Effect of the experimental conditions on 1 the product selectivity", Applied Catalysis A: General, Elsevier Science, Amsterdam, NL vol. 384, No. 1-2, Aug. 20, 2010, oages 115-121.
Umansky B et al.: "Banish the benzene, boost the octane", Hydrocarbon Engineering, Palladian Publications, Farnham, GB, vol. 12, Jan. 1, 2007, pp. 61-62.
El-Mekki El Malki, Michael Clark: "BenzOUT Reducing Benzene Enhancing Gasoline Product Value", NPRA Conference, Phoenix, AZ, Mar. 21-23, 2010; XP00263211.
Pierre Leprince: "Le raffinage du petrole-3.Procédés de Transformation", Jan. 1, 1998, Technip, Paris, XP002670362, vol. 3.
The International Search Report and the Written Opinion of the International Searching Authority issued in related international application No. PCT/US2011/062626.
The International Search Report and the Written Opinion of the International Searching Authority issued in related international application No. PCT/US2011/023904.
The International Search Report and the Written Opinion of the International Searching Authority issued in related international application No. PCT/US2011/062635.
The International Search Report and the Written Opinion of the International Searching Authority issued in corresponding international application No. PCT/US2011 /062648.

* cited by examiner

*Primary Examiner* — Thuan D Dang
(74) *Attorney, Agent, or Firm* — Roberts Mlotkowski; Safran & Cole, P.C.

(57) ABSTRACT

A process is disclosed for alkylating benzene contained in a benzene-containing refinery gasoline stream also comprising at least 0.1 wt % of at least one C6 to C8 olefin. In the process, the refinery gasoline stream is contacted under alkylation conditions with an alkylating agent selected from one or more C2 to C5 olefins in at least a first alkylation reaction zone and a second alkylation reaction zone connected in series to produce an alkylated effluent, which has reduced benzene content as compared with said refinery gasoline stream. All of the refinery gasoline stream is introduced into the first alkylation reaction stage, whereas an aliquot of the alkylated effluent is recycled and introduced to the second, but not the first, alkylation reaction zone.

13 Claims, 1 Drawing Sheet

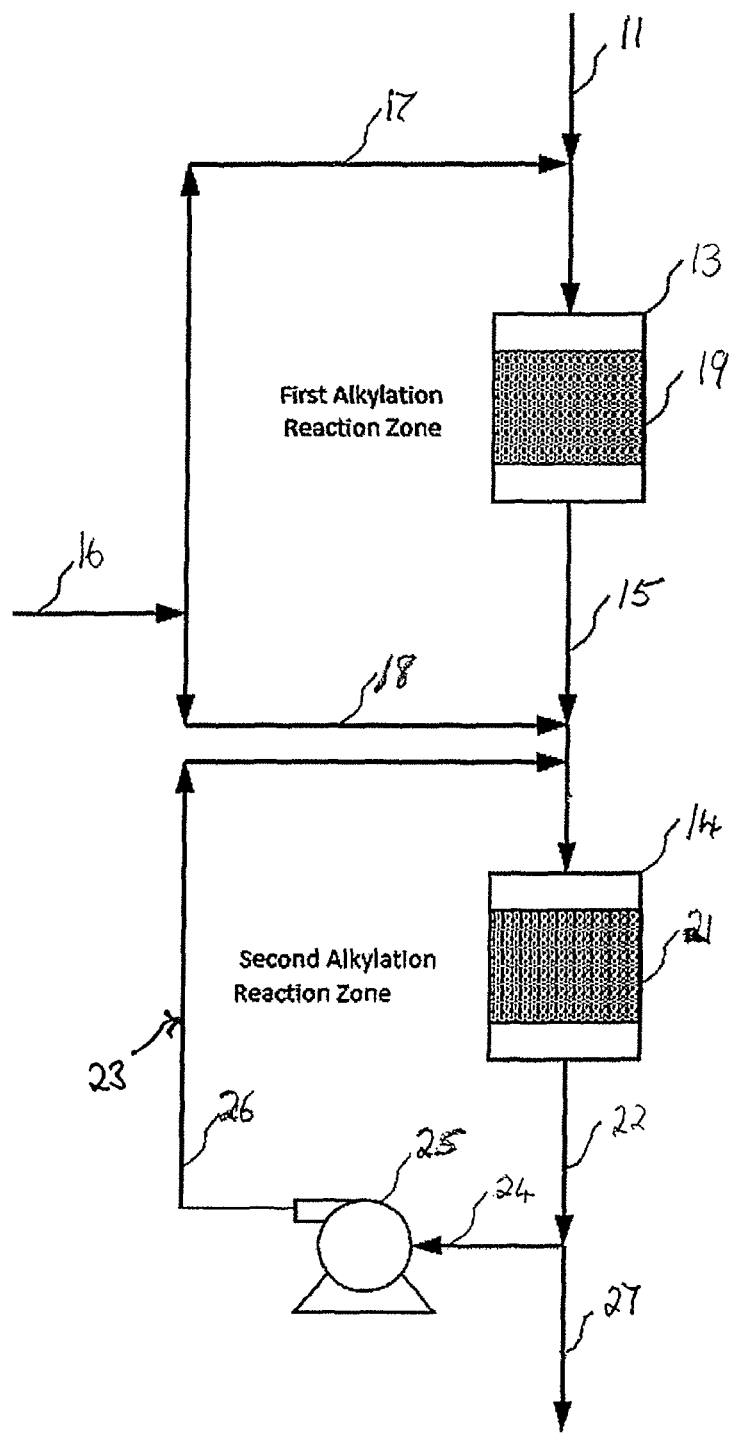

PROCESS FOR REDUCING THE BENZENE CONTENT OF GASOLINE

CROSS-REFERENCE TO RELATED APPLICATIONS

The present Application is a U.S. National Phase of international application PCT/US2011/062648 filed on Nov. 30, 2011 which claims priority of the filing date of PCT/US2011/023912 filed on Feb. 7, 2011. The disclosure of the international application PCT/US2011/062648 is hereby incorporated by reference into the present Application.

FIELD

This invention relates to a process for reducing the benzene content of gasoline.

BACKGROUND

Benzene is considered to be environmentally hazardous. As a result, the State of California and the United States Environmental Protection Agency have instituted regulations to limit the amount of benzene which may be present in gasoline. As of January 2011, the US MSAT-2 (Mobile Source Air Toxics) regulation requires reduction of this annual average benzene content in gasoline to no greater than 0.62 volume %.

One known route for reducing the benzene content of gasoline is to selectively alkylate the benzene using a lower olefin. For example, Holtermann et al U.S. Pat. No. 5,149,894 describes a process for converting benzene to alkylated benzenes in a gasoline blend stock. The process involves contacting a benzene-containing gasoline blend stock with a C2 to C4 olefin stream in the presence of a catalyst containing the zeolite, SSZ-25, to produce an alkylated light hydrocarbon stream with reduced benzene content.

Cheng et al. U.S. Pat. No. 5,545,788 describes a process for the production of a more environmentally suitable gasoline by removing a substantial portion of benzene in gasoline by alkylation of reformate. The process involves alkylation using a light olefin feed at low temperature over the zeolite catalyst, MCM-49.

Umansky el al. U.S. Pat. No. 7,476,774 describes a process where light olefins including ethylene and propylene are extracted from refinery off-gases, such as from a catalytic cracking unit, into a light aromatic stream, such as a reformate containing benzene and other single ring aromatic compounds, which is then reacted with the light olefins to form a gasoline boiling range product containing alkylaromatics. The alkylation reaction is carried out in the liquid phase with a catalyst which preferably comprises a member of the MWW family of zeolites, such as MCM-22, using a fixed catalyst bed.

However, in addition to limiting the benzene level in gasoline, current and ongoing regulations restrict the content of residue, which consists of heavy hydrocarbon components with boiling points outside the gasoline boiling range. The US standard specification for automotive spark-ignition engine fuel (ASTM D4814) requires that the residue (heavies) in the gasoline product is no more than 2 volume %. As benzene regulations become more stringent, meeting the heavies level becomes an increasing problem because the light olefins used to alkylate the benzene in the gasoline can undergo undesirable competing reactions, such as olefin oligomerization to produce, for example, C6 to C8 olefins. Subsequent aromatic alkylation reactions result in the formation of heavy components, with boiling points outside of the typical gasoline boiling range. This problem is particularly pronounced with gasoline feeds which contain significant quantities of C6 to C8 olefins since these olefins further contribute towards the production of heavy hydrocarbons boiling above the gasoline range.

According to the present invention, it has now been found that the undesirable formation of heavy components in the alkylation of benzene-containing gasoline streams containing significant quantities of C6 to C8 olefins can be reduced by introducing a once-through alkylation pre-reactor upstream of a main recirculating alkylation reactor.

SUMMARY

In one aspect, the invention resides in an process for alkylating benzene contained in a benzene-containing refinery gasoline stream, such as a reformate or a light naphtha, said process comprising contacting said benzene-containing refinery gasoline stream under alkylation conditions with an alkylating agent selected from one or more C2 to C5 olefins in at least a first alkylation reaction zone and a second alkylation reaction zone connected in series to produce an alkylated effluent, which has reduced benzene content as compared with said refinery gasoline stream, wherein all of the refinery gasoline stream is introduced into the first alkylation reaction stage, wherein an aliquot of the alkylated effluent is recycled and introduced to the second, but not the first, alkylation reaction zone, and wherein the refinery gasoline stream comprises at least 0.1 volume % of at least one C6 to C8 olefin.

Conveniently, the alkylated effluent contains at least 50% less, such as at least 75% less, for example at least 87% less, benzene as compared with said refinery gasoline stream.

Conveniently, the weight ratio of recycled alkylated effluent to feed introduced into said second alkylation reaction stage is at least 0.05.

Typically, the refinery gasoline stream comprises at least 4 volume % benzene and the alkylated effluent comprises less than 2 volume %, such as less than 0.62 volume %, benzene. Generally, the alkylated effluent comprises no more than 2 volume % of compounds having a boiling point greater than 236° C. at atmospheric pressure.

In one embodiment, the contacting in the at least one alkylation reaction zone takes place in the presence of a catalyst comprising an MWW zeolite and the alkylating agent is propylene.

The refinery gasoline stream may be substantially in the liquid phase during said contact of the refinery gasoline stream with the alkylating agent in the alkylation reaction zone.

BRIEF DESCRIPTION OF THE DRAWINGS

FIG. 1 is a schematic diagram of a process for reducing the benzene content of gasoline in accordance with one embodiment of the invention.

DETAILED DESCRIPTION OF THE EMBODIMENTS

Refinery streams which may be alkylated to decrease benzene content include streams comprising benzene and alkylbenzenes. Examples of such streams include reformates and naphtha streams, especially light naphtha streams (typically boiling in the range from about 40° C. to about 150° C.). Blends of refinery streams may also be alkylated. The refinery streams employed in the present process typically comprise at least 4 volume % benzene, such as from 4 volume % to 40 volume % benzene.

Reformates have high octane number attributable to their high aromatics content. However, high concentrations of benzene in reformate, e.g., in excess of 4 volume %, can limit reformate utility as a blending component where environmental considerations require low benzene levels in gasoline product. Various efforts to reduce benzene content in reformate, e.g., selective hydrogenation, high temperature fluid-bed MBR, and reformate alkylation with methanol all suffer from octane losses or total liquid product losses associated with undesired cracking of C5+ non-aromatics.

The present invention relates to a process whereby benzene-containing reformates and other refinery streams are treated to reduce benzene content by alkylation. Undesirable alkylation of higher boiling aromatics, such as xylenes, may be minimized.

Examples of suitable alkylating agents for use in the present process are olefins having 2 to 5 carbon atoms, such as ethylene, propylene, butenes, and pentenes. Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, and FCC off-gas, etc., are useful alkylating agents herein. Compositions of examples of olefin containing streams suitable for use as alkylating agents are described, for example, in U.S. Pat. No. 7,476,774.

The alkylation process may be conducted such that the organic reactants, i.e., the alkylatable aromatic compound and the alkylating agent, are brought into contact with a zeolite catalyst composition under alkylation conditions effective to produce an alkylated effluent which has reduced benzene content as compared with said refinery gasoline stream and is essentially free (that is contains less than 0.1 wt %) of the alkylating agent. Generally, the alkylated effluent contains at least 50% less, such as at least 75% less, for example at least 87% less, benzene as compared with said refinery gasoline stream.

Suitable alkylation conditions may include a temperature of from about 0° C. to about 500° C., for example, between about 50° C. and about 300° C., and a pressure of from about 0.2 to about 250 atmospheres, for example, from about 1 to about 50 atmospheres. The feed weight hourly space velocity (WHSV) will generally be between 0.1 hr$^{-1}$ and 500 hr$^{-1}$, for example, from 0.5 hr$^{-1}$ to 100 hr$^{-1}$. The latter WHSV is based upon the total weight of active catalyst (and binder if present).

The alkylation process is conducted in at least two alkylation reaction zones which are connected in series and which each typically contain a fixed bed of the catalyst composition. All of the refinery gasoline stream is introduced into the first alkylation reaction zone, while the C2 to C5 alkylating agent is supplied, generally in equal amounts, to each alkylation reaction zone. An aliquot of the alkylated effluent is recycled to the second, but not the first, alkylation reaction zone. Generally, weight ratio of recycle to feed at the inlet of said second alkylation reaction zone is at least 0.05:1, such as from about 0.1:1 to about 10:1.

As used herein, the term "aliquot" is used in its commonly accepted sense to mean a portion of the alkylated effluent, which has not been subjected to fractionation or other operations to alter its composition and so has the same composition as the total effluent.

The reactants may be in the vapor phase or the liquid phase or in a mixture of liquid and vapor phases. The reactants may be neat, i.e., free from intentional admixture or dilution with other material, or they can be brought into contact with the zeolite catalyst composition with the aid of carrier gases or diluents such as, for example, hydrogen or nitrogen.

One embodiment of the present process is shown in FIG. 1, in which a gasoline feed containing benzene and at least one C6 to C8 olefin is supplied by line 11 to a first alkylation reaction zone 13, which is connected in series to a second alkylation reaction zone 14 by line 15. Propylene is supplied to the process through line 16 and is divided equally between, and fed to, the reaction zones 13, 14 by lines 17, 18 respectively.

The first and second alkylation reaction zones 13, 14 each house a fixed bed of alkylation catalyst 19, 21 and the outlet of the second alkylation zone 14 is connected to the inlet of zone 14 by line 22 and a recycle loop 23 comprising line 24, pump 25 and line 26.

In practice, the first alkylation reaction zone 13 is maintained under conditions such that part of the benzene in the gasoline feed reacts with the propylene introduced into zone 13 through line 17 mainly to produce cumene. The partially alkylated gasoline product then exits the zone 13 and is transported by line 15 to the second alkylation reaction zone 14, which is also maintained under conditions such that part of the benzene in the gasoline feed reacts with the propylene introduced through line 18 again mainly to produce cumene. The alkylated effluent then exits the second alkylation zone 14 through line 22 and part of the effluent is recovered via line 27 for use as a gasoline blending stock and part is recycled to the inlet of the second alkylation reaction zone 14 by recycle loop 23.

Catalyst System

The catalyst system used in the alkylation of the present process is preferably one based on a zeolite of the MWW family because these catalysts exhibit excellent activity for the desired aromatic alkylation reaction using light olefins, especially propylene. It is, however, possible to use other molecular sieve catalysts for this alkylation, including catalysts based on ZSM-12 as described in U.S. Pat. Nos. 3,755,483 and 4,393,262 for the manufacture of petrochemical cumene from refinery benzene and propylene or catalysts based on zeolite beta as described in U.S. Pat. No. 4,891,458, all of which are reported to have activity for the alkylation of light aromatics by propylene.

MWW Zeolite

The MWW family of zeolite materials has achieved recognition as having a characteristic framework structure which presents unique and interesting catalytic properties. The MWW topology consists of two independent pore systems: a sinusoidal ten-member ring [10 MR] two dimensional channel separated from each other by a second, two dimensional pore system comprised of 12 MR super cages connected to each other through 10 MR windows. The crystal system of the MWW framework is hexagonal and the molecules diffuse along the [100] directions in the zeolite, i.e., there is no communication along the c direction between the pores. In the hexagonal plate-like crystals of the MWW type zeolites, the crystals are formed of relatively small number of units along the c direction as a result of which, much of the catalytic activity is due to active sites located on the external surface of the crystals in the form of the cup-shaped cavities. In the interior structure of certain members of the family such as MCM-22, the cup-shaped cavities combine together to form a supercage. The MCM-22 family of zeolites has attracted significant scientific attention since its initial announcement by Leonovicz et al. in Science 264, 1910-1913 [1994] and the later recognition that the family includes a number of zeolitic materials such as PSH 3, MCM-22, MCM-49, MCM-56, SSZ-25, ERB-1, ITQ-1, and others. Lobo et al. AIChE Annual Meeting 1999, Paper 292J.

The relationship between the various members of the MCM-22 family have been described in a number of publications. Significant members of the family are MCM-22, MCM-36, MCM-49, and MCM-56. When initially synthesized from a mixture including sources of silica, alumina, sodium, and hexamethylene imine as an organic template, the initial product will be MCM-22 precursor or MCM-56, depending upon the silica: alumina ratio of the initial synthesis mixture. At silica:alumina ratios greater than 20, MCM-22 precursor comprising H-bonded vertically aligned layers is produced whereas randomly oriented, non-bonded layers of MCM-56 are produced at lower silica:alumina ratios. Both these materials may be converted to a swollen material by the use of a pillaring agent and on calcination, this leads to the laminar, pillared structure of MCM-36. The as-synthesized MCM-22 precursor can be converted directly by calcination to MCM-22 which is identical to calcined MCM-49, an intermediate product obtained by the crystallization of the randomly oriented, as-synthesized MCM-56. In MCM-49, the layers are covalently bonded with an interlaminar spacing slightly greater than that found in the calcined MCM-22/MCM-49 materials. The as-synthesized MCM-56 may be calcined itself to form calcined MCM-56 which is distinct from calcined MCM-22/MCM-49 in having a randomly oriented rather than a laminar structure. In the patent literature MCM-22 is described in U.S. Pat. No. 4,954,325 as well as in U.S. Pat. Nos. 5,250,777; 5,284,643 and 5,382,742. MCM-49 is described in U.S. Pat. No. 5,236,575; MCM-36 in U.S. Pat. No. 5,229,341 and MCM-56 in U.S. Pat. No. 5,362,697.

A preferred zeolitic material for use as the MWW component of the catalyst system is MCM-22 or MCM-49.

Catalyst Matrix

In addition to the zeolitic component, the catalyst will usually contain a matrix material or binder in order to give adequate strength to the catalyst as well as to provide the desired porosity characteristics in the catalyst. High activity catalysts may, however, be formulated in the binder-free form by the use of suitable extrusion techniques, for example, as described in U.S. Pat. No. 4,908,120. When used, matrix materials suitably include alumina, silica, silica alumina, titania, zirconia, and other inorganic oxide materials commonly used in the formulation of molecular sieve catalysts. For use in the present process, the level of zeolite, such as MCM-22 or ZSM-5 type (intermediate pore size) zeolite, in the finished matrixed catalyst will be typically from 20 to 70% by weight, and in most cases from 25 to 65% by weight. In manufacture of a matrixed catalyst, the active ingredient will typically be mulled with the matrix material using an aqueous suspension of the catalyst and matrix, after which the active component and the matrix are extruded into the desired shape, for example, cylinders, hollow cylinders, trilobe, quadlobe, etc. A binder material such as clay may be added during the mulling in order to facilitate extrusion, increase the strength of the final catalytic material and to confer other desirable solid state properties. The amount of clay will not normally exceed 10% by weight of the total finished catalyst. Unbound (or, alternatively, self-bound) catalysts are suitably produced by the extrusion method described in U.S. Pat. No. 4,582,815, to which reference is made for a description of the method and of the extruded products obtained by its use. The method described there enables extrudates having high constraining strength to be produced on conventional extrusion equipment and accordingly, the method is suitable for producing the catalysts which are silica-rich. The catalysts are produced by mulling the zeolite with water to a solids level of 25 to 75 wt % in the presence of 0.25 to 10 wt % of basic material such as sodium hydroxide. Further details are to be found in U.S. Pat. No. 4,582,815.

Gasoline Product

Even with a refinery gasoline feed comprising at least 4 volume % benzene, the present process allows the production of a gasoline product which contains less than 2 volume %, typically less than 0.62 volume %, benzene and generally no more than 2 volume % of compounds having a boiling point greater than 236° C. at atmospheric pressure. In addition, it is to be appreciated that, unlike conventional processes for alkylating aromatics with C2 to C5 olefins, the entire alkylated product of the present process is intended for use as a gasoline blending component, without fractionation to separate the product into monoalkylated species, polyalkylated species and unreacted aromatic feed.

The invention will now be more particularly described with reference to the following non-limiting Examples.

COMPARATIVE EXAMPLE 1

A sample of MCM-49 alkylation catalyst was tested with a feed containing 15% benzene, 4% toluene, 1% 1-hexene and 80% n-heptane. Propylene was used as the alkylating agent. In one embodiment of the invention, a single stage alkylation reactor was used as the base case to represent an alkylation reaction system, with a reactor inlet temperature of 200° C., and with a reactor effluent recycle to feed recirculation ratio of 4:1.

EXAMPLE 2

An alkylation pre-reactor was placed upstream of the alkylation reaction system of the base case described in Comparative Example 1. The data listed in Table 1 below show that a once-through pre-reactor placed upstream of the main circulating reactor reduces the heavies make substantially.

The benefit of a combination of an alkylation pre-reactor with any other configuration of the alkylation reaction system is possible and a similar benefit in reduced heavies make is projected.

TABLE 1

| Reactor Configuration | Benzene Conversion | Heavies Make (volume %) |
|---|---|---|
| 1-Stage Circulating Reactor (Comparative Example 1) | 75% | 1.3% |
| | 87% | 2.1% |
| | 93% | 3.2% |
| | 97% | 5.5% |
| Once-Through Pre-Reactor Followed By 1-Stage Circulating Reactor (Example 2) | 84% | 1.2% |
| | 90% | 1.8% |
| | 95% | 3.2% |

What is claimed is:

1. A process for reducing the benzene content of gasoline by alkylating benzene contained in a benzene-containing refinery gasoline stream, said process comprising contacting said benzene-containing refinery gasoline stream under alkylation conditions with an alkylating agent selected from one or more C2 to C5 olefins in at least a first alkylation reaction zone and a second alkylation reaction zone connected in series to produce an alkylated effluent, which has reduced benzene content as compared with said refinery gasoline stream, wherein all of the refinery gasoline stream is introduced into the first alkylation reaction stage, wherein an aliquot of the alkylated effluent from the second alkylation zone is recycled and introduced to the second, but not the first, alkylation reaction zone, and wherein the refinery gasoline stream comprises at least 0.1 wt. % of at least one C6 to C8 olefin.

2. A process according to claim 1, wherein the alkylated effluent contains at least 50% less benzene as compared with said refinery gasoline stream.

3. A process according to claim 1, wherein the alkylated effluent contains at least 75% less benzene as compared with said refinery gasoline stream.

4. A process according to claim 1, wherein the alkylated effluent contains at least 87% less benzene as compared with said refinery gasoline stream.

5. A process according to claim 1, wherein the weight ratio of recycled alkylated effluent to feed introduced into said second alkylation reaction stage is at least 0.05.

6. A process according to claim 1, wherein said refinery gasoline stream is a reformate or a light naphtha.

7. A process according to claim 1, wherein said alkylating agent is propylene.

8. A process according to claim 1, wherein said refinery gasoline stream comprises at least 4 volume % benzene.

9. A process according to claim 1, wherein said alkylated effluent comprises less than 2 volume % benzene.

10. A process according to claim 1, wherein said alkylated effluent comprises less than 0.62 volume % benzene.

11. A process according to claim 1, wherein said alkylated effluent comprises no more than 2 volume % of compounds having a boiling point greater than 236° C. at atmospheric pressure.

12. A process according to claim 1, wherein the alkylation reaction in each of said first and second alkylation reaction zones takes place in the presence of a catalyst comprising an MWW zeolite.

13. A process according to claim 1, wherein said refinery gasoline stream is substantially in the liquid phase during said contacting.

\* \* \* \* \*